United States Patent
Oprea et al.

(10) Patent No.: US 9,839,912 B2
(45) Date of Patent: Dec. 12, 2017

(54) ANALYTICAL DEVICE WITH BASE MODULE AND EXCHANGEABLE CASSETTE

(71) Applicant: Endress + Hauser Conducta Gesellschaft für Mess- und Regeltechnik mbH + Co. KG, Gerlingen (DE)

(72) Inventors: Michael Oprea, Stuttgart (DE); Thomas Baumgartner, Stuttgart (DE); Jurgen Erchinger, Konigsfeld (DE); Christian Hirn, Leonberg (DE); Ralf Steuerwald, Eberdingen (DE); Tobias Zachmann, Stuttgart (DE); Ulrich Kathe, Ludwigsburg (DE); Anja Gerlinger, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 510 days.

(21) Appl. No.: 13/792,286

(22) Filed: Mar. 11, 2013

(65) Prior Publication Data

US 2013/0243651 A1    Sep. 19, 2013

(30) Foreign Application Priority Data

Mar. 16, 2012 (DE) .................. 10 2012 102 256

(51) Int. Cl.
*B01L 3/00* (2006.01)
*G01N 21/78* (2006.01)
(Continued)

(52) U.S. Cl.
CPC .............. *B01L 3/508* (2013.01); *B01L 3/523* (2013.01); *B01L 3/563* (2013.01); *G01N 33/18* (2013.01);
(Continued)

(58) Field of Classification Search
CPC .......... B01L 3/563; B01L 3/508; B01L 3/523; B01L 2300/123; B01L 2400/0616;
(Continued)

(56) References Cited

U.S. PATENT DOCUMENTS

| 4,664,149 A | 5/1987 | Fremy |
| 5,099,883 A | 3/1992 | Maiville |

(Continued)

FOREIGN PATENT DOCUMENTS

| AT | 43693 E | 8/1910 |
| CN | 101443591 A | 5/2009 |

(Continued)

OTHER PUBLICATIONS

German Search Report dated Oct. 24, 2012, issued in Application No. 10 2012 102 256.9. , in Munich, Germany.

*Primary Examiner* — Jill Warden
*Assistant Examiner* — Julie Tavares
(74) *Attorney, Agent, or Firm* — Christopher R. Powers; PatServe (57) ABSTRACT

An analytical device for automated determining of a measured variable of a liquid sample, includes: a base module; a replaceable cassette connectable with the base module and having at least one liquid container connectable via a fluid line with a measuring cell and containing a reagent to be added to the liquid sample for forming a measured liquid; and a measuring transducer for registering measured values correlated with the measured variable for the measured liquid accommodated in the measuring cell. The cassette has, associated with the at least one liquid container, a fluid coupling apparatus having a primary component and a secondary component and serving for producing a connection of the fluid line with the liquid container.

14 Claims, 8 Drawing Sheets

(51) Int. Cl.
  *G01N 35/10*   (2006.01)
  *G01N 33/18*   (2006.01)

(52) U.S. Cl.
  CPC ..... *G01N 35/1002* (2013.01); *G01N 35/1097* (2013.01); *B01L 3/527* (2013.01); *B01L 2200/026* (2013.01); *B01L 2300/123* (2013.01); *B01L 2400/0616* (2013.01); *B01L 2400/0633* (2013.01); *G01N 21/78* (2013.01)

(58) Field of Classification Search
  CPC ............ B01L 2400/0633; B01L 3/527; B01L 2202/026; G01N 35/1097; G01N 33/18; G01N 35/1002; G01N 21/78
  USPC ..... 422/82.05, 63, 68.1, 544, 538; 73/64.55, 73/64.56; 436/174
  See application file for complete search history.

(56) References Cited

U.S. PATENT DOCUMENTS

| | | | |
|---|---|---|---|
| 5,816,668 | A | 10/1998 | Heubner |
| 6,378,908 | B1 | 4/2002 | Walker et al. |
| 2006/0266425 | A1 | 11/2006 | Erath et al. |
| 2009/0159825 | A1 | 6/2009 | Trimborn et al. |
| 2009/0278347 | A1 | 11/2009 | Kerin et al. |
| 2010/0052315 | A1 | 3/2010 | Kerin et al. |
| 2011/0212538 | A1* | 9/2011 | Lundgreen ......... G01N 21/3151 436/164 |
| 2012/0173164 | A1 | 7/2012 | Steuerwald et al. |
| 2012/0198921 | A1* | 8/2012 | Lundgreen et al. ......... 73/61.41 |

FOREIGN PATENT DOCUMENTS

| | | | |
|---|---|---|---|
| CN | 101482571 A | 7/2009 | |
| DE | 40 30 294 A1 | 4/1991 | |
| DE | 691 22 772 T2 | 3/1997 | |
| DE | 195 33 482 A1 | 4/1997 | |
| DE | 197 16 980 A1 | 10/1998 | |
| DE | 199 02 707 A1 | 7/2000 | |
| DE | 103 13 484 A1 | 10/2004 | |
| DE | 600 22 725 T2 | 6/2006 | |
| DE | 10 2005 045 154 A1 | 3/2007 | |
| DE | 10 2009 020 561 A1 | 11/2009 | |
| DE | 10 2009 038 995 A1 | 3/2010 | |
| DE | 10 2009 001 737 A1 | 9/2010 | |
| DE | 20 2010 005 868 U1 | 9/2010 | |
| DE | 10 2009 029 305 A1 | 3/2011 | |
| EP | 2 233 750 A2 | 9/2010 | |
| EP | 2 016 324 B1 | 7/2011 | |
| WO | 2007/131569 A1 | 11/2007 | |
| WO | WO2010040657 A1 * | 4/2010 | |
| WO | WO 2011029698 A1 * | 3/2011 | ............ G01N 35/08 |
| WO | WO 2011035959 A1 * | 3/2011 | |

\* cited by examiner

ANALYTICAL DEVICE WITH BASE MODULE AND EXCHANGEABLE CASSETTE

TECHNICAL FIELD

The invention relates to an analytical device for automated determining of a measured variable of a liquid sample.

BACKGROUND DISCUSSION

Such analytical devices are applied, for example, in process measurements technology, in environmental technology, automatic analytical devices and in industrial measurements technology. For example, analytical devices can serve for monitoring and optimizing the cleaning effectiveness of a clarification plant, e.g. for monitoring activation basins and the clarification plant outlet. Furthermore, analytical devices can be applied for monitoring drinking water or for quality monitoring of food. Measured and monitored is, for example, the content in the liquid sample of a certain substance, which is also referred to as the analyte. Analytes can be, for example, ions, such as ammonium, phosphate, silicate or nitrate, biological or biochemical compounds, e.g. hormones, or even microorganisms. Other measured variables, which are determined by analytical devices in process measurements technology, especially in the field of monitoring water, include total organic carbon content (TOC) and chemical oxygen demand (COD). Analytical devices can be embodied, for example, as cabinet devices or as buoys.

Frequently in analytical devices, the sample to be analyzed is treated by mixing-in one or more reagents, so that a chemical reaction can occur in the liquid sample. Preferably, the reagents are so selected that the chemical reaction is detectable by means of physical methods, for example, by optical measurements, by means of potentiometric or amperometric sensors or by measuring conductivity. For example, the chemical reaction can bring about a coloring or a color change, which is detectable with optical means. The color intensity is, in this case, a measure for the measured variable to be determined. The measured variable can be ascertained, for example, photometrically, in that electromagnetic radiation, for example, visible light, is radiated from a radiation source into the liquid sample and after transmission through the liquid sample is received by a suitable receiver. The receiver produces a measurement signal dependent on the intensity of the received radiation, from which the measured variable can be derived.

In order to use such analytical methods in an automated fashion, for example, for industrial applications or for monitoring a clarification plant or an outdoor body of water, it is desirable to provide an analytical device, which performs the required analytical method in an automated fashion. The most important requirements for such an analytical device are, besides a sufficient accuracy of measurement, robustness, simple serviceability and the assurance of a sufficient working, and environmental safety.

Automatic analytical devices are known from the state of the art. Thus, for example, DE 102 22 822 A1, DE 102 27 032 A1 and DE 10 2009 029305 A1 disclose online analyzers for analyzing samples. These online analyzers are embodied, in each case, as cabinet devices, which include a control unit, liquid containers for reagents, standard solutions and cleaning liquids, pumps for transporting and dosing, or metering, liquid samples, and the one or more reagents, into a measuring cell, and measuring transducers for optical measurements on the liquid sample contained in the measuring cell and treated with the one or more reagents. The reagents, standard solutions or cleaning liquids are transported from the liquid containers and into the measuring cell. Correspondingly, used liquid is transferred from the measuring cell into a waste container. If the waste container or one or more of the reagent supply containers must be replaced, attention must be paid that the hose connections then are connected back correctly. The hoses and the transport pumps are susceptible to material fatigue and must likewise be subjected to maintenance or replaced from time to time.

Described in DE 10 2009 029 305 A1 is an analytical device for automated determining of a measured variable of a liquid sample. The analytical device has one or more liquid containers for one or more liquids, e.g. reagents, a measuring cell for accommodating a measured liquid produced by mixing the liquid sample with one or more reagents and a measuring transducer for providing one or more measurement signals correlated with the measured variable. The analytical device possesses, moreover, a control unit for control of the analytical device and for determining the measured variable based on the measuring signals provided by the measuring transducer. Additionally, the analytical device includes a processing unit controlled by the control unit. The processing unit includes a supply- and dosing system for supplying and metering the liquid sample and liquids from the liquid storage units into the measuring cell. The analytical device possesses at least one replaceable cassette, into which the liquid containers and/or at least parts of the processing unit are integrated.

An advantage of this embodiment is that the liquid containers or wear parts of the processing unit, e.g. hoses, flexible tubing or wear parts of the supply- and dosing system, which must be replaced from time to time by the operating personnel, can be arranged in the cassette. A service person must then, for providing new liquids or for replacing wear parts, only remove the "used" cassette having the liquid containers, or wear parts, and put in a new cassette.

The cassette described in DE 10 2009 029 305 A1 provides, in an embodiment, a housing surrounding the liquid containers, wherein there are integrated in a wall of the housing, for closing the cassette liquid tightly in the state separated from the remaining parts of the analytical device, closeable connectors, which, for example, interact with complementary connectors of liquid lines arranged outside the cassette for forming fluid couplings, in order to connect the liquid containers integrated in the cassette with the external liquid lines. In this embodiment, a number of liquid containers can, without additional effort, be connected, for example, to a processing module arranged outside the cassette. The fluid couplings between the cassette and the outwardly lying liquid lines comprise thus a primary side arranged in or on the cassette and a secondary side interacting therewith and arranged outside the cassette, e.g. in an adapter mounted outside of the cassette. Disadvantageous in such a fluid coupling is that assuring the proper arrangement of the primary and secondary sides of the different fluid couplings relative to one another for implementing the fluid tight connections requires, in the case of connecting the cassette to the analytical device, very complex guiding means for assuring precise orientation of the primary sides relative to the secondary sides. Additionally, there is the danger that the connectors arranged in the outer wall of the cassette can be damaged during transport of the cassette.

SUMMARY OF THE INVENTION

It is an object of the invention to overcome the disadvantages of the state of the art.

This object is achieved by an analytical device for automated determining of a measured variable of a liquid sample, comprising:

a base module;

a replaceable cassette connectable with the base module and having at least one liquid container connectable via a fluid line with a measuring cell and containing a reagent to be added to the liquid sample for forming a measured liquid;

a measuring transducer for registering measured values correlated with the measured variable for the measured liquid accommodated in the measuring cell. The cassette has, associated with the at least one liquid container, a fluid coupling apparatus having a primary component and a secondary component and serving for producing a connection of the fluid line with the liquid container.

Since the cassette has both the primary component as well as also the secondary component of the fluid coupling apparatus, the correct orientation of the primary and secondary components of the one or more fluid coupling apparatuses relative to one another in the case of connecting the cassette to the base module does not, as in the state of the art, have to be assured by complex, highly precise, guiding means. In a preferred embodiment, the two components are arranged within the cassette. In this way, also the danger of damage of the primary or secondary component, e.g. in the case of transport or replacement of the cassette, is prevented.

The connection producible by the fluid coupling apparatus is preferably fluid-tight, especially sealed to liquid, so that leakages in the case of transport of a fluid, or a liquid, between the liquid container and the measuring cell via the fluid coupling apparatus in the connected state are prevented.

The primary component and the secondary component each have an interface, via which they can be connected with one another for forming a fluid coupling. The primary component or the secondary component can be connected to the at least one liquid container on its respective end facing away from the interface. This connection can especially be formed via a fluid line, e.g. a hose or tubing. For this, the primary or secondary component can have, for example, a Luer connector. Since the liquid containers and the primary component, respectively secondary component, connected, especially via a fluid line, with the liquid container, are associated with the cassette, and preferably are arranged within the cassette housing, destruction of the liquid container, the fluid line and the fluid coupling in the case of transport or due to difficult environmental conditions is prevented.

The base module and the cassette can be embodied as separate components, especially with each having its own outer housing enclosing the components of the base module, respectively the components of the cassette, and each housing includes complementary mechanical connecting means for producing a releasable connection between the cassette and the base module. The cassette can include locking means to prevent movement of the secondary component relative to the primary component of the at least one fluid coupling apparatus, when the cassette is not connected with the base module, and to enable movement of the secondary component relative to the primary component, upon the connecting of the cassette with the base module.

The base module can have a drive, especially actuatable by hand or automatically, which is embodied to bring about a movement of the secondary component and the primary component relative to one another for providing a connection, preferably a fluid tight connection, between the secondary component and the primary component. The movement of the secondary component and the primary component relative to one another for producing a connection is preferably triggered automatic upon the mechanical connecting of the cassette with the base module, i.e. automatically triggered and/or driven without other measures provided by a service person. In this way, a "plug and play" functionality can be achieved. The automatic or hand operable drive can be embodied, for example, to be actuated purely mechanically, upon producing the connection of the cassette with the base module, especially without an additional energy source.

The primary component of the fluid coupling apparatus can, in an embodiment, comprise a cartridge-shaped housing having front and rear openings, wherein the rear opening is connected with the liquid container, especially via another fluid line, and wherein, on the front opening, a sealing seat is formed, on which lies a sealing element arranged in the housing interior to close the front opening liquid tightly, when the primary component is not connected with the secondary component.

The associated secondary component of the fluid coupling apparatus can have a cartridge-shaped plug, which is embodied to enter into the front opening of the housing of the primary component for producing a connection between the cartridge-shaped plug of the secondary component and the cartridge-shaped housing of the primary component and, in such case, to lift the sealing element from the sealing seat. The outer diameter of the plug is at least sectionally so matched to an inner diameter of the front housing opening of the primary component that the outer wall of the plug and the inner wall of the housing opening contact one another fluid-tightly, especially liquid tightly. In given cases, a seal can be provided supplementally.

The cassette can have a plurality of liquid containers, with which are associated, in each case, a fluid coupling apparatus having a primary component and a secondary component, in order to produce a connection, preferably a fluid tight connection, between the respective liquid containers and a line for conveying fluid to the measuring cell, when the cassette is connected with the base module, wherein the primary components are mounted on a first carrier and the secondary components on a second carrier movable relative to the first carrier. The liquid containers can be embodied, for example, as flexible bags.

The carriers can be embodied as carrier blocks movable relative to one another, to which the particular component of the at least one fluid coupling apparatus is mounted in a predetermined orientation. If the cassette has a plurality of liquid containers and a plurality of associated fluid coupling apparatuses, their primary components, respectively secondary components, can, for example, be arranged secured beside- or on top of one another on the carrier blocks.

It can be required to withdraw individual liquid containers from the cassette, for example, in the context of checking- or maintenance measures. In order to be able to withdraw a primary or secondary component connected with a liquid container and fluid-tightly closing such, together with the liquid container, from the cassette, the primary or secondary component can have a gripping element, for example, a protrusion, a bracket, a flange or the like, in order to facilitate the removal of the primary or secondary component from its carrier, on which it is mounted.

The first and second carriers have guiding means preferably engaging one another for guiding a relative movement of the first and second carriers achieving a connection, especially a liquid tight connection, of the carrier-mounted primary and secondary components of the fluid coupling apparatuses.

The measuring cell can be arranged in the base module. In this case, the base module can have fluid lines, which extend from the measuring cell to a fluid interface between the base module and the cassette. The fluid interface between base module and cassette can be formed, for example, by a passageway communicating with the fluid line and opening in a wall of the base module, which, in the case of cassette connected with the base module, adjoins a complementary passageway opening in a wall of the cassette and communicating with a fluid line of the cassette.

The analytical device can furthermore comprise at least one supply- and dosing system for transport of liquid from a liquid container into the measuring cell and/or from the measuring cell into a liquid container, and a control system, which is embodied to control the at least one supply- and dosing system and/or, based on measuring signals provided by the measuring transducer, to ascertain measured values of the measured variable.

Additionally, the analytical device can have a sample taking- and sample preparation system, which is embodied to withdraw a liquid sample from a liquid to be monitored, to filter such and/or to pretreat it in some other manner, before the at least one reagent is added to it.

If a plurality of liquid containers are present, these can contain, besides the reagents to be added to the liquid sample, also cleaning liquids or calibration standards. Furthermore, an option is that some liquid containers serve for accommodating waste products, e.g. used liquid samples, cleaning liquids or calibration standards.

The liquid containers can be embodied, for example, as plastic pouches, which are connected, in each case, with a primary component of a fluid coupling apparatus via a fluid line embodied, for example, in the form of a plastic tube. So long as the cassette is not connected with the base module, the primary component closes the plastic pouch liquid tightly. Only when a connection between primary and secondary component is produced, can liquid be transported from the respective liquid container to the measuring location, or in the reverse direction, through the fluid coupling apparatus. Preferably, the primary component and the secondary component are formed of materials, which are chemically inert relative to the liquids contained in the liquid containers, respectively not chemically attacked by these. Thus, suitable materials for the primary component and the secondary component include, for example, polymer materials, such as e.g. fluoroelastomers, such as FPM, respectively FKM (fluorinated rubber), PTFE (polytetrafluoroethylene) or polyethylene (PE).

The invention relates, moreover, to a fluid coupling apparatus comprising:

a primary component, which includes a cartridge-shaped housing having front and rear openings, wherein, on the front opening, a sealing seat is formed, on which lies a sealing element arranged in the housing interior to close the front opening liquid tightly; and, connectable with the primary component, a secondary component, which has a cartridge-shaped plug, which is embodied to enter into the front opening of the housing of the primary component for producing a liquid tight connection between the cartridge-shaped plug of the secondary component and the cartridge-shaped housing of the primary component and, in such case, to lift the sealing element from the sealing seat.

This fluid coupling apparatus can be applied in this or in one of the embodiments described in the following in an analytical device according to one of the above described embodiments. It is, however, not limited to this application and can be applied in a large number of other applications.

In an embodiment, the housing of the primary component tapers on its front end for forming the seal seat. A press part arranged in the interior of the housing and bearing on its rear side against an annular shoulder formed within the housing presses the sealing element against the sealing seat.

The sealing element can be essentially spherically shaped. The advantages of this shape of the sealing element lie in the facts that, on the one hand, the sealing element lifted from the sealing seat in the connected state of the fluid coupling apparatus can be easily flowed around by fluid transported through the fluid coupling, and, on the other hand, its assembly is easy, so that automated manufacturing of the primary component is facilitated.

The housing of the primary component can have a tapering section in a rear end region, wherein, on the housing wall, there is arranged, extending radially into the housing interior, at least one rib, which, in the case of connected primary and secondary components, prevents the sealing element lifted from the sealing seat from closing the rear opening of the housing of the primary component. Advantageously, there are on the housing wall of the tapering section at least three ribs arranged extending radially into the housing interior, so that the sealing element lifted from the sealing seat is held as centrally as possible within the housing of the primary component and so is more easily flowed around.

The shell shaped plug of the secondary component can have a cavity, which, in the case of connected primary and secondary components, is located within the housing of the primary component and prevents the sealing element lifted from the sealing seat from closing the rear opening of the housing of the secondary component.

The primary component can have on its housing exterior a radially extending grip. As already described above, such a grip facilitates removal of the primary component, with a thereto connected fluid line connecting the primary component with a liquid container, from a carrier or other mounting, in which the primary component can be accommodated as specified.

BRIEF DESCRIPTION OF THE DRAWINGS

The invention will now be described in greater detail based on the examples of embodiments illustrated in the appended drawing, the figures of which show as follows.

DETAILED DISCUSSION IN CONJUNCTION WITH THE DRAWINGS

Figure 1:
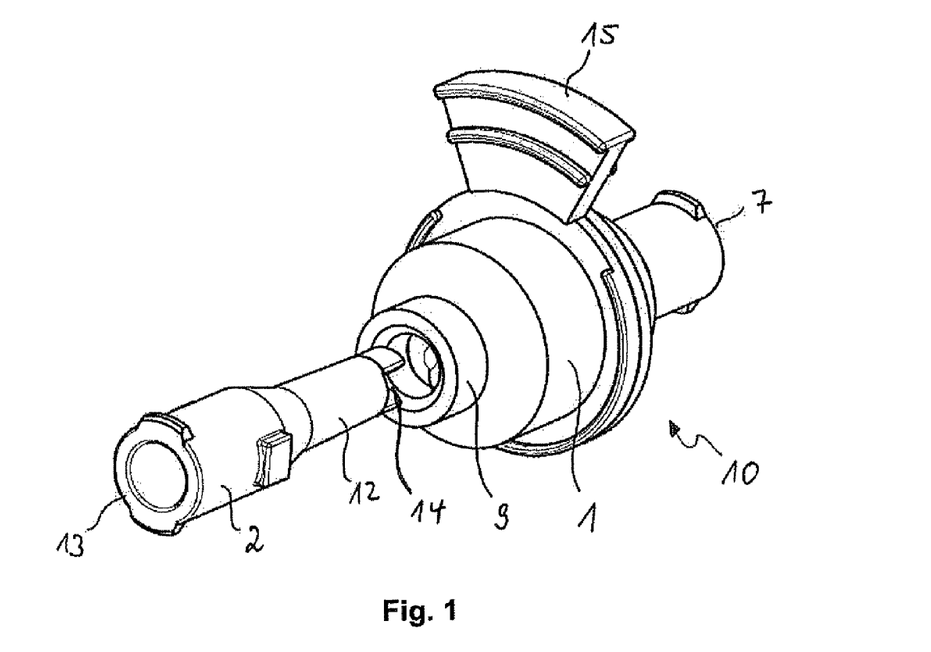
FIG. 1 is a fluid coupling apparatus having a primary component and a secondary component.

FIG. 1 shows a fluid coupling apparatus 10 having a primary component 1 and a secondary component 2. A corresponding longitudinal section view is provided in FIG. 2. The primary component 1 includes a cartridge-shaped housing, which, in the example shown here, is composed of a first housing part 3 and a second housing part 4. The two housing parts 3 and 4 can be connected with one another, for example, by ultrasonic welding or by means of other methods of material bonding. The cartridge-shaped housing includes a front opening and a rear opening. Toward the front opening, the diameter of the first housing part 3 tapers for forming a seal seat 8, against which a spherical sealing element 5 arranged in the interior of the housing lies. A press part 6 serves to press the sealing element 5 against the sealing seat 8, so that the front opening of the housing of the primary component is closed fluid-tightly, especially liquid tightly, by the sealing element 5. An annular end face of the second housing part 4 engaging rearwardly in the first housing part forms a radial shoulder, against which the press part 6 is rearwardly axially supported.

Figure 2:
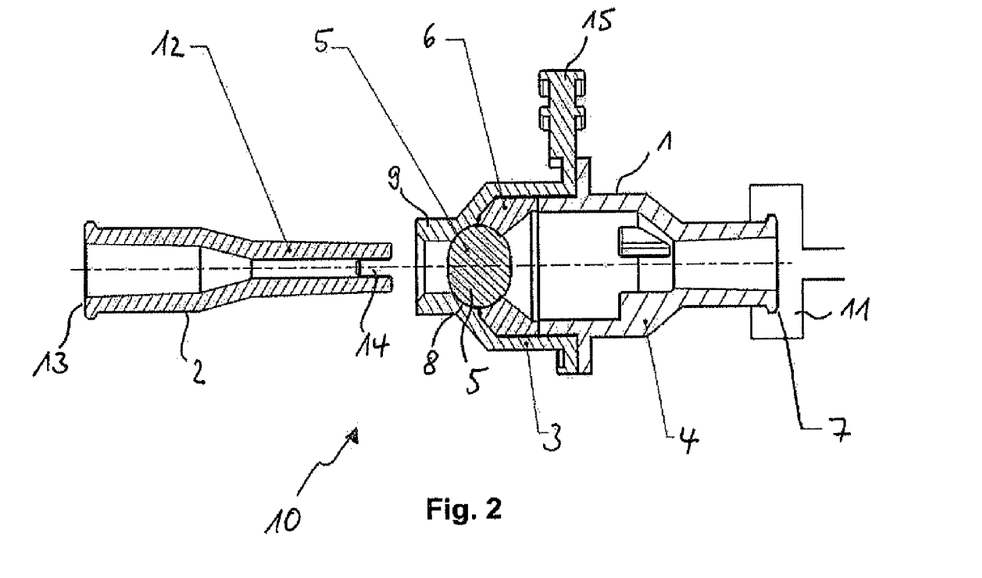
FIG. 2 is the fluid coupling apparatus in a longitudinal section view in the unconnected state.

On its front, the first housing part 3 includes a section 9 of lesser diameter forming the front opening of the housing. This section 9 serves for accommodating the secondary component 2 of the fluid coupling apparatus 1 for providing a fluid tight, hydraulic connection between the primary and secondary components. The second housing part 4 includes rearwards a connector 7, at which a fluid line 11 is connected, for example, a fluid line 11 embodied as a hose, or flexible tubing. Connector 7 can be embodied, for example, as a Luer taper. For easier handling, the primary component 1 includes on its outside a radially extending, gripping element 15.

The secondary component 2 includes at its front end a cartridge-shaped plug 12, whose outer diameter is matched in such a manner to the inner diameter of the front section 9 of the first housing part 3 of the primary component 1 that the plug 12 is introducible into such for providing a fluid tight, especially liquid tight, connection between the primary and secondary components. Plug 12 includes on its front one or more axially extending slots 14. To the rear, the secondary component 2 includes a connector 13, which is connectable with a fluid line, especially a hose or tubing.

Figure 3:
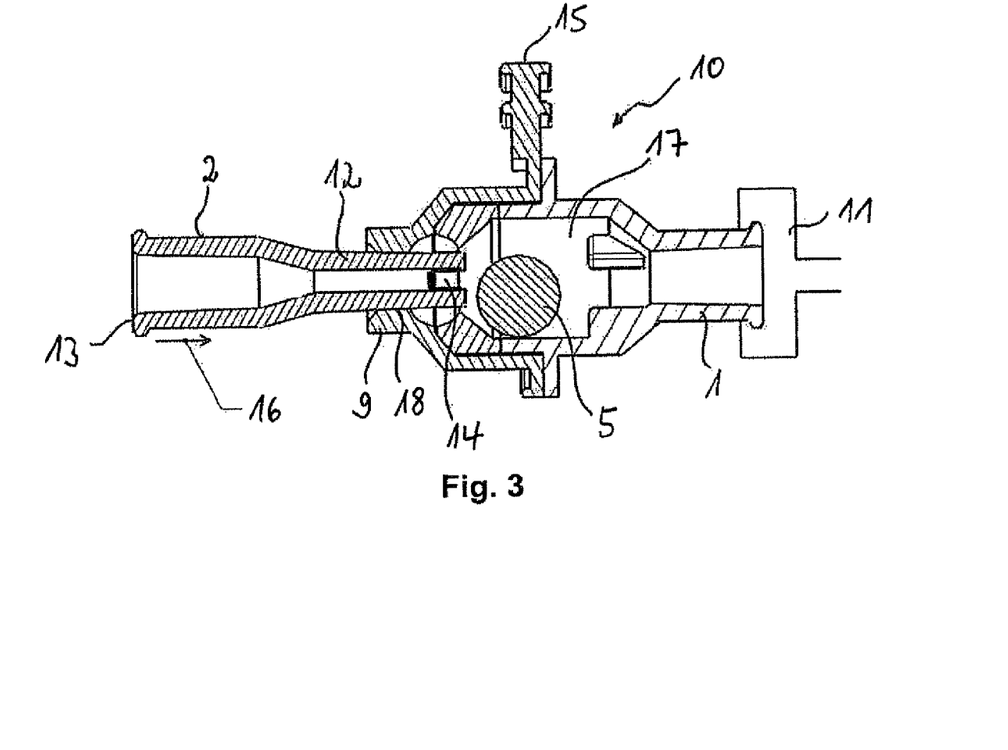
FIG. 3 is the fluid coupling apparatus in a longitudinal section view in the connected state.

FIG. 3 shows the fluid coupling apparatus 10 in the connected state. For producing a hydraulic connection between the primary component 1 and the secondary component 2, the secondary component 2 is shifted axially relative to the primary component 1 with the force 16. In such case, the plug 12 lifts the sealing element 5 from its sealing seat 8. The sealing element 5 is thereby squeezed into the housing interior 17 of the primary component 1. As already mentioned, the outer diameter of the plug 12 is so matched to the inner diameter of the front housing section 9 of the primary component 1 that the outer wall of the plug 12 and the inner wall of the section 9 in the connected state contact one another on the interface 18 fluid-tightly, especially liquid tightly. In given cases, an additional seal can be provided for sealing the interface 18.

Figure 4:
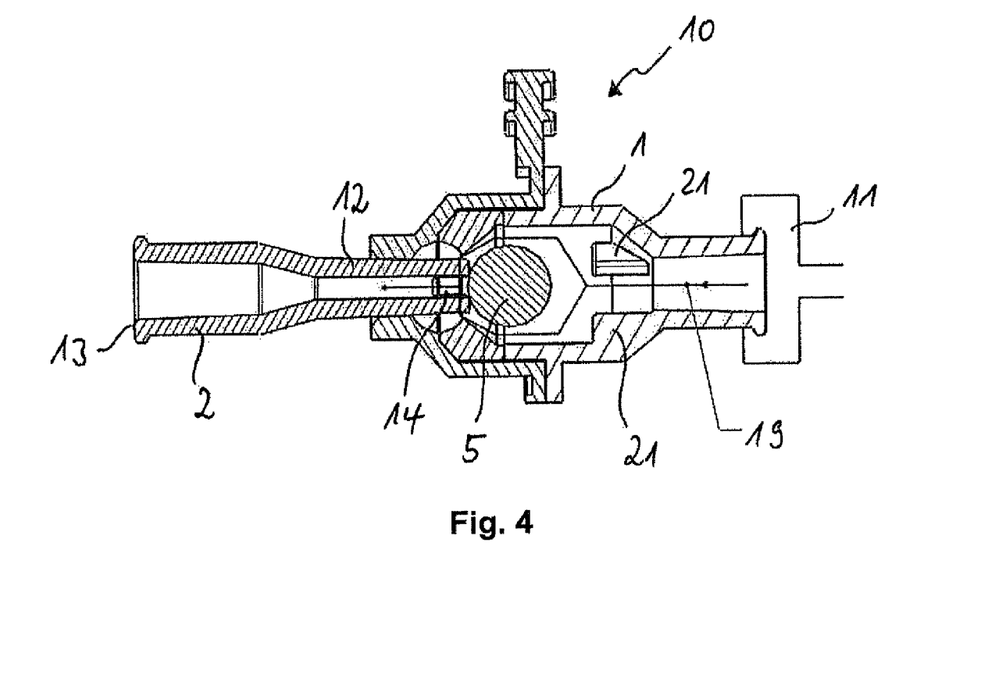
FIG. 4 is the fluid coupling apparatus in a longitudinal section view in the connected state with representation of a liquid flow from the primary component to the secondary component.
Figure 5:
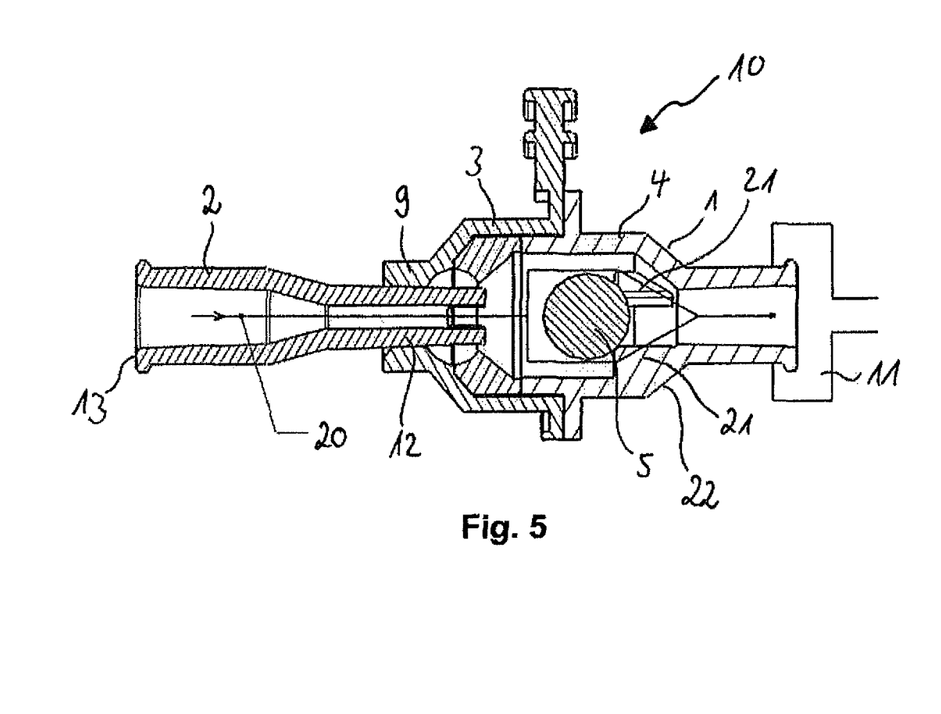
FIG. 5 is the fluid coupling apparatus in a longitudinal section view in the connected state with representation of a liquid flow from the secondary component to the primary component.

In the connected state of the fluid coupling apparatus 10, fluid, especially liquid, can flow axially through it. This is illustrated in FIGS. 4 and 5 in greater detail. FIG. 4 shows with the arrows 19 a fluid flow through the fluid coupling apparatus 10 from the hose 11 toward the rear connector 13 of the secondary component 2. The fluid flows around the spherically shaped sealing element 5 and presses it against the end of the plug 12. The fluid can, however, flow via the slots 14 past the sealing element 5 into the housing interior of the secondary component 2 in the direction of the rear connector 13 of the secondary component 2.

FIG. 5 shows with the arrows 20 a fluid flow through the fluid coupling apparatus 10 in the opposite direction. Also in this direction, the sealing element 5 located in the housing interior of the primary component cannot block the flow. This is the result of three radially inwardly projecting ribs 21 arranged in a tapering end region 22 of the second housing part 4. The three ribs 21 center the sealing element 5 in the housing interior 17, so that the fluid can flow around the sealing element 5.

The fluid coupling apparatus 10 is suitable for connecting two liquid carrying lines, e.g. two hoses or two lengths of tubing. Preferably, the coupling apparatus is formed of materials, which are inert relative to the fluids or liquids flowing through it. If the liquids are aqueous solutions, acids or alkaline solutions, suitable materials for housing parts of the primary component 1 and the secondary component 2 include, for example, polymer material, such as polyethylene (PE), polytetrafluoroethylene (PTFE), polypropylene (PP) and polyvinylidene fluoride (PVDF). Suitable material for sealing element 5 is a fluoroelastomer, such as FPM, or FKM.

The fluid coupling apparatus 10 shown in FIGS. 1 to 5 can be applied advantageously in an analytical device, which serves for automated determining of a measured variable of a liquid sample, for example, in one of the initially described applications.

Figure 6:
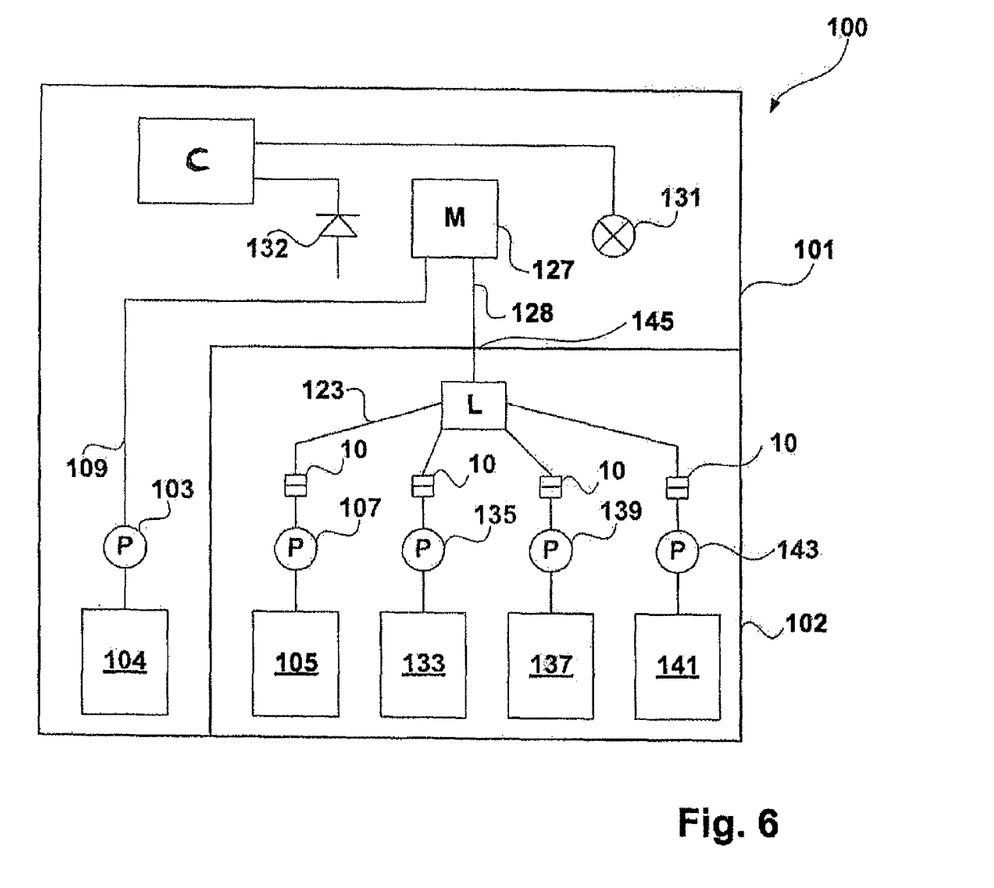
FIG. 6 is a schematic representation of an analytical device for automated determining of a measured variable of a liquid sample and having a base module and a replaceable cassette connectable with the base module.

FIG. 6 shows such an analytical device 100 schematically. Analytical device 100 includes a plurality of liquid containers 133, 137 and 141, a processing system with a plurality of pumps 135, 139 and 143 for supplying and metering liquids contained in the liquid containers 133, 137 and 141, and liquid lines, via which the liquid containers 133, 137, 141 are connected with a measuring cell 127. Additionally, the analytical device 100 includes a waste container 105, which likewise is connected via a pump 107 with the measuring cell 127. The measuring cell 127 is, in the example shown here, preceded by a valve system L ("liquid manager"), which serves to control the supply of the individual liquids from the liquid containers 133, 137 and 141, respectively the draining of used liquid from the measuring cell 127 into the waste container 105. Valve system L connects the liquid containers 133, 137 and 141 via the liquid line 128 with the measuring cell 127. The pumps 107, 135, 139 and 143 can be, for example, membrane pumps, piston pumps, especially syringe pumps, or peristaltic pumps.

Furthermore, the analytical device 100 includes a sample supply 104, in which the sample liquid is stored temporarily after removal from a sampling location, for example, an open body of water. For performing an analysis, a liquid sample of predetermined volume is removed from the sample supply 104 and transported via the supply line 109 by means of the pump 103 into the measuring cell 127. Pump 103 can be embodied, as in the case of the other pumps 107, 135, 139, 143, for example, as a membrane pump, a piston pump, especially as a syringe pump, or as a peristaltic pump.

For registering the measured variable to be determined by the analytical device 100, the analytical device 100 includes an optical measuring transducer, which includes a radiation source 131 and a receiver 132, which are so arranged relative to the measuring radiation transparent measuring cell 127 that the measuring radiation passes from the source 131 through a liquid sample contained in the measuring cell 127 and then strikes the receiver 132. Depending on measurement task, the analytical device 100 can, of course, also have other than an optical measuring transducer—for example, an electrical or electrochemical, measuring transducers.

The analytical device 100 can be operated in a completely automated fashion. For this, it possesses a control unit C, which, in the example shown here, also performs the functions of an evaluating unit, especially determining a measured variable based on a measured value registered by the measuring transducer. Control unit C includes a data processing system and a memory, in which one or more operating programs are stored, which serve for control of the analytical device 100 and/or control of the sample preparation system 1, as well as, in given cases, evaluation of the measurement signals delivered by the optical measuring transducer 131, 132. The data processing system can also include an input apparatus for input of commands or parameters by a service person and/or an interface for the receipt of commands, parameters or other data from a superordinated unit, for example, from a process control system. Additionally, the control unit C can also include an output apparatus for output of data, especially measurement results, or operating information, to a user or even include an interface for output of data to the superordinated unit. Control unit C is connected with drives of the pumps 103, 107 135, 139, 143 and with valve system L, in order to operate such for transporting liquids from the sample collecting unit and the liquid containers 133, 137 and 141 into the measuring cell 127 in an automated fashion. The control unit C is, moreover, connected with the measuring transducer, in order to control such and to ascertain the measured variable from measurement signals of the receiver 132.

Analytical device 100 includes a base module 101 and a replaceable cassette 102 connectable with the base module 101. Base module 101 and cassette 102 are embodied as separate components each with its own housing. In the example shown here, the base module contains the sample supply 104 as well as the measuring cell 127, the optical measuring transducer 131, 132 and the control unit C. The pump drives for the pumps 103, 107, 135, 139 and 143 can likewise be contained in the base module 101. Cassette 102 contains the liquid containers 105, 133, 137 and 141, the pumps 107, 135, 139 and 143 as well as the valve system L. A hydraulic interface 145 permits the liquid transport via the valve system L between the cassette 102 and the measuring cell 127 arranged in the base module 101. The liquid containers 105, 133, 137 and 141 contained in the cassette 102 are connected via fluid coupling apparatuses 10, which can be embodied with the valve system L as described based on FIGS. 1 to 5, wherein both the primary component 1 as well as also the secondary component 2 of the fluid coupling apparatuses 10 are arranged within the cassette 102.

In other, equally possible embodiments, the measuring cell and/or the measuring transducer can likewise be contained in the replaceable cassette. In another embodiment, also the sample supply can be contained in the cassette. Conversely, it is also an option that one or more other liquid containers, which, in the example shown here, are contained in the replaceable cassette, are placed in the base module.

So long as the replaceable cassette 102 is not connected with the base module 101, the primary component 1 and the secondary component 2 of the fluid coupling apparatuses 10 are separated from one another. The primary components 1 connected with respective liquid containers 105, 133, 137, 141 are, in this state, liquid tightly sealed by a sealing element. Cassette 102 includes a drive to be described in greater detail based on FIGS. 7 to 12. Upon connection of the cassette 102 with the base module 101, the drive automatically produces a connection of the primary components 1 with the associated secondary components 2, so that automatically a liquid tight connection of the lines leading to the valve system L from the liquid containers 105, 133, 137, 141 via the fluid coupling apparatuses 10 is produced, without that the service person connecting the cassette 102 with the base module 101 need assure the correct connection of the liquid containers to the corresponding liquid lines to the valve system L and therewith to the measuring cell 127. In other words, this is a "plug and play" system.

Liquid container 141 can contain a reagent, which is mixed with the liquid sample for treating such. If the measured variable to be determined is, for example, the concentration of an analyte in the liquid, the reagent can be so selected that it reacts with the analyte to form a colored reaction product. The intensity of the color is then a measure for the concentration to be determined. The wavelength of the measuring radiation transmitted from the radiation source 131 is, in this case, matched to the color of the reaction product and is correspondingly evaluated by the receiver 132, respectively the control unit C. Instead of a single reagent as in the example shown here, depending on measured variable to be determined, also a plurality of reagents can be applied. In this case, the analytical device 100 has a corresponding number of liquid containers for the required reagents.

In measurement operation of the analytical device 100, the control unit C first doses a predetermined amount of the sample liquid contained in the sample collecting unit 7 into the measuring cell 127 as liquid sample to be analyzed. At the same time, or thereupon, the control unit C controls the pump 143, in order to transport a predetermined amount of the reagent contained in the liquid container 141 into the measuring cell. Measuring cell 127 serves thus in the here described example also as mixing cell, in which the liquid sample and reagent are mixed with one another. There are, however, also other embodiments possible, in which the reagent or a plurality of reagents for treating the liquid sample are mixed with one another before the liquid sample treated by means of the reagents is metered into the measuring cell 127.

For registering the measured variable to be determined for the treated liquid sample contained in the measuring cell, the control unit C operates the measuring transducer 131, 132 and evaluates the measurement signal output by the measuring transducer 131, 132. The measured variable ascertained from the measurement signal by the control unit C can be stored in a data memory of the control unit, and/or output via an interface to a superordinated unit and/or via a display of the control unit C.

After determining the measured variable, the measuring cell 127 is emptied by transporting the used liquid sample contained in the measuring cell by means of the pump 107 into the waste container 105. The analytical device 100 has other liquid containers 133, 137, which can contain standard solutions for calibrations and/or cleaning solutions for cleaning. By means of the pumps 135, 139 associated with liquid containers 133, 137, their solutions can be transported into the measuring cell 127.

After one or more completed measuring cycles, a calibrating of the analytical device can be performed by transporting a calibration standard from the liquid container 137 into the measuring cell 127. The calibration standard is treated, like a "real" liquid sample from the sample supply, in the measuring cell 127 with reagent transported by means of pump 143 from the liquid container 141 into the measuring cell 127. By means of the measuring transducer 131, 132, a measured value of the measured variable is photometrically determined and, in given cases, based on the measured value known for the calibration standard, an adjusting of the analytical device 100 is performed.

Figure 7:
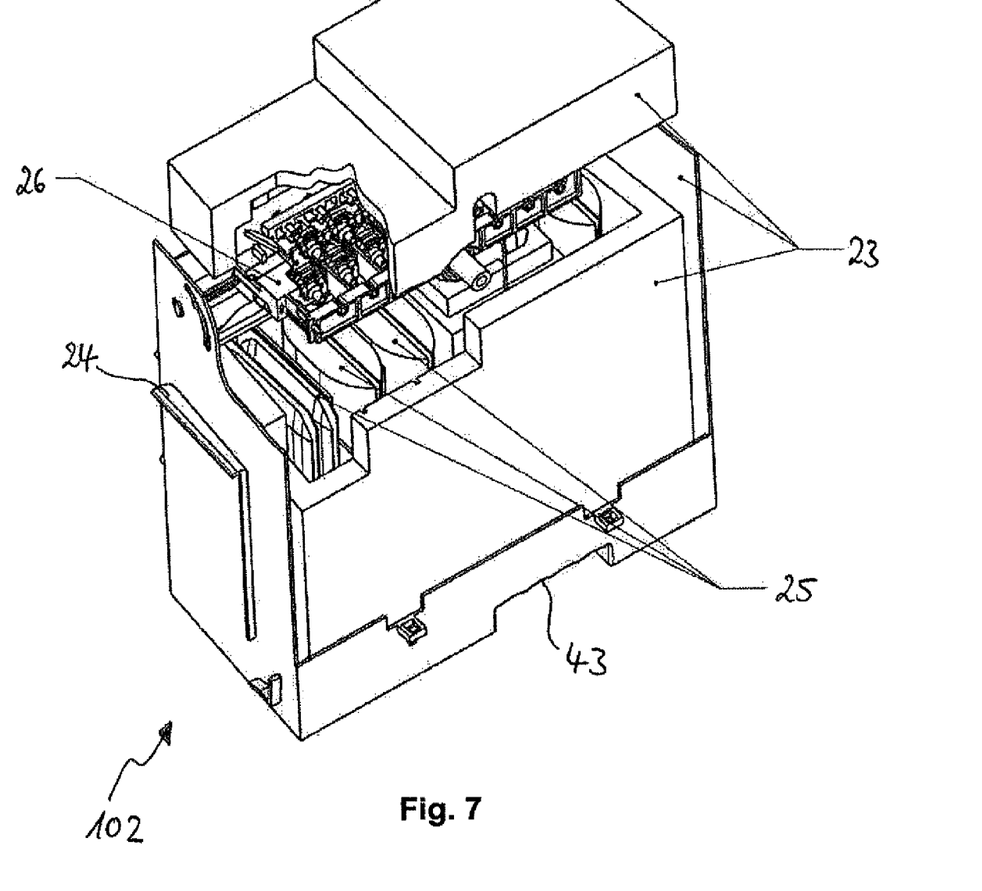
FIG. 7 is a cassette for an analytical device according to FIG. 6.

An embodiment of a replaceable cassette of the analytical device 100 schematically illustrated in FIG. 6 will now be described in greater detail based on FIGS. 7 to 12. FIG. 7 shows the cassette 102, which has a housing 23, whose dimensions are those required for connection with a determined base module (not shown) of an analytical device. The housing can especially have guiding means, which interact with complementary guiding means of the base module, in order to assure that the cassette can be connected with the base module only in a predetermined orientation relative to the base module. Arranged on the housing 23 for easier handling are grips 24 and a grip cavity 43.

Arranged in the lower region of the cassette housing 23 are liquid containers 25 embodied as bags. In the upper region of the cassette 102 is located a carrier apparatus 26, on which are mounted a plurality of fluid coupling apparatuses 10. In the example shown here, the liquid pouches, or bags, are connected via fluid lines (not shown), e.g. hoses or flexible tubing, in each case, with a primary component 1 of a fluid coupling apparatus, in an embodiment, according to FIGS. 1 to 5. So long as the cassette 102 is still not connected with the base module of the analytical device, the openings of the primary components 1 facing away from the associated liquid containers 25 are liquid tightly closed by the sealing element 5, so that no liquid can escape from the liquid containers 25 outwardly into the cassette 102 or into the environment. If the cassette 102 is connected with the base module 101, then, as to be explained below in greater detail, automatically a connection between the primary and secondary components of the fluid coupling apparatus 10 is produced, so that liquid can be transported from the liquid containers 25 via the fluid coupling apparatuses 10 into the valve system L and from there into the measuring cell 127 of the analytical device 100 (FIG. 6).

Figure 8:
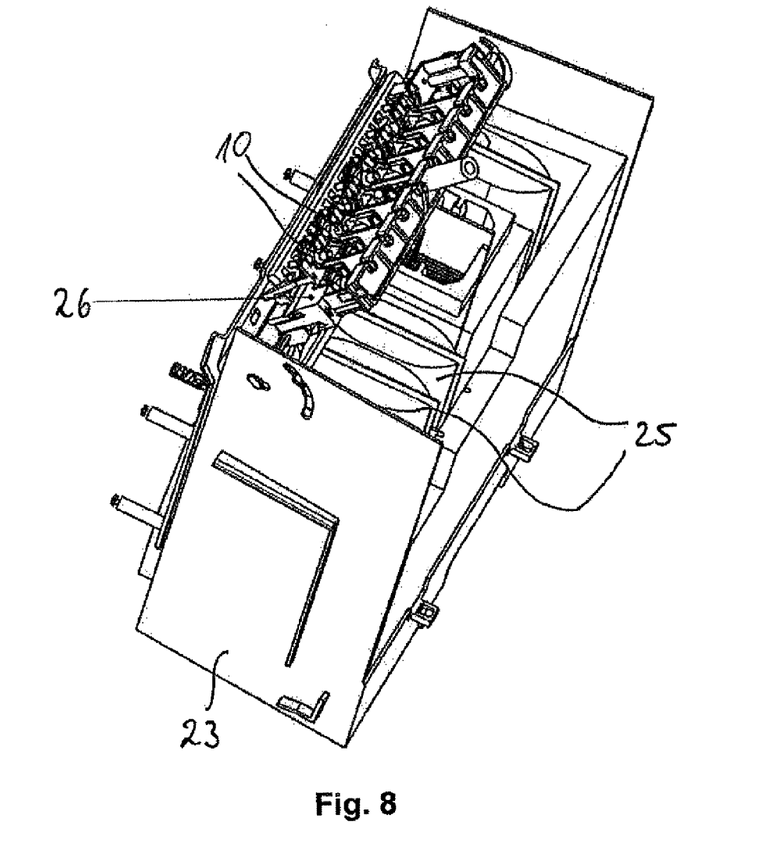
FIG. 8 is the cassette in an opened state.

FIG. 8 shows the cassette 102 in an opened state. In this state, the cassette 102 can be checked or subjected to maintenance, for example, individual bags can be removed for examination or for refilling. For this, the carrier apparatus 26 can be tilted upwardly about an axle arranged in its rear region, in order to make the fluid coupling apparatuses 10 arranged on the carrier apparatus 26 and the liquid containers 25 more easily accessible.

Figure 9:
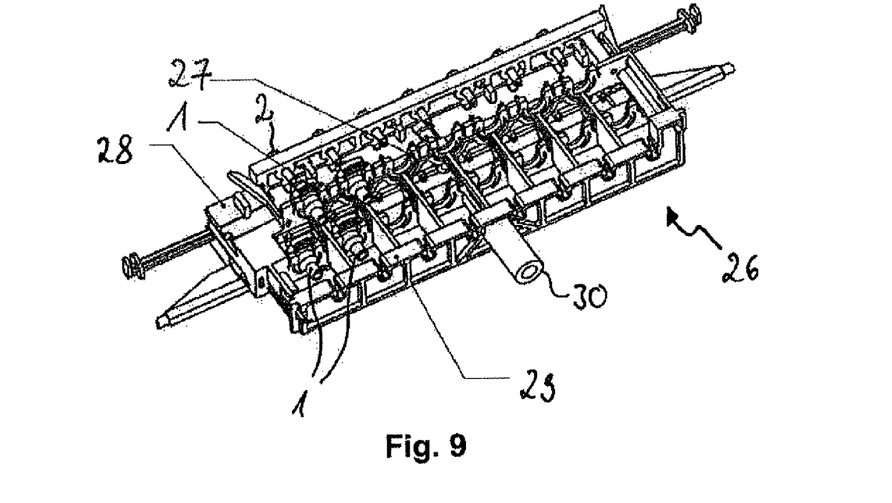
FIG. 9 is a detail view of a carrier apparatus accommodated in the cassette and having a plurality of locations for mounting primary components and secondary components of fluid coupling apparatuses.
Figure 10:
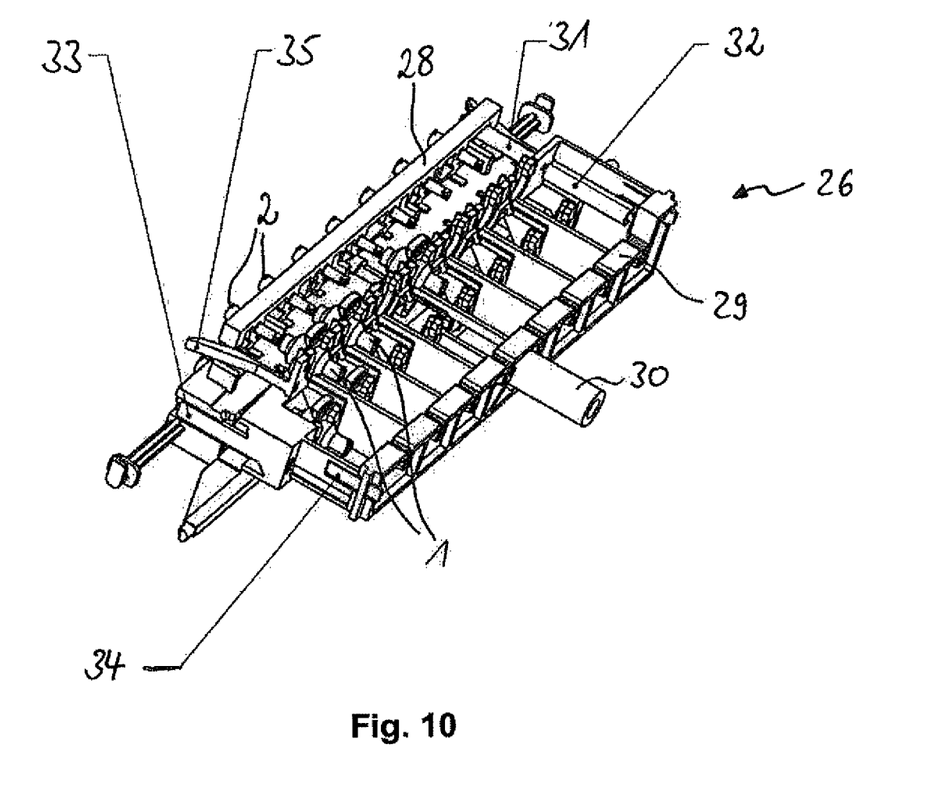
FIG. 10 is a view of the carrier apparatus illustrated in FIG. 9 from another angle of sight.
Figure 11:
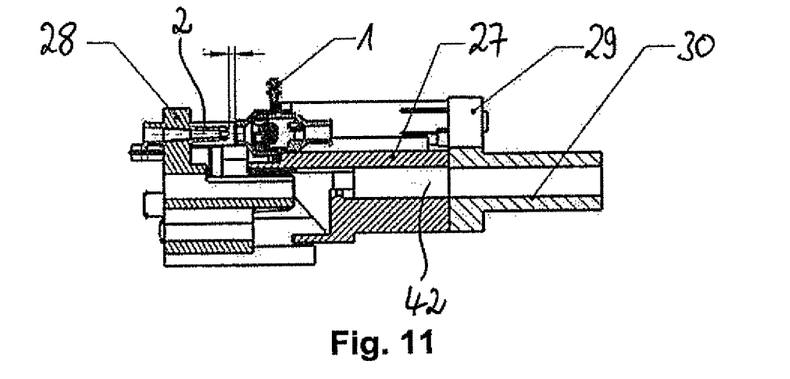
FIG. 11 is a cross sectional view of the carrier apparatus.

The carrier apparatus 26 is shown in detail in FIGS. 9 and 10 from different viewing angles and in FIG. 11 in cross section. The carrier apparatus 26 includes a first carrier block 27 and a second carrier block 28, which are arranged to be movable relative to one another. The first carrier block 27 includes, in the example shown here, 15 berths, at which primary components 1 of fluid coupling apparatuses 10 of FIG. 1 can be mounted. In the example shown here, the first carrier block contains only four primary components 1. Mounted on the second carrier block 28 are the secondary components 2 of the fluid coupling apparatuses 10 lying opposite the primary components 1. Also the second carrier block 28 has 15 berths, at which the secondary components 2 corresponding to the primary components 1 mounted on the first carrier block 27 can be mounted.

The first carrier block 27 is shiftable relative to the second carrier block 28 parallel to the axes of the fluid coupling apparatuses 10, in order to move the primary components 1 onto the secondary components 2. This movement is precisely guided by cylindrical guides 31, 32 connected with the first and second carrier blocks 27.

Two snap fits 33, two snap fits 34 and two levers 35 prevent inadvertent relative shifting movement between the two carrier blocks 27, 28, when the cassette 102 is not connected with the base module, e.g. during transport or during storage of the cassette 102. The snap fits 33 and 34 will allow relative movement between blocks 27 and 28, after a certain level of force is exerted for moving blocks 27 and 28 toward one another. Levers 35 are pivotable. In a "secured" position, an undercut edge of each lever 35 engages a nose, so that the blocks 27 and 28 cannot be moved toward one another.

Figure 12:
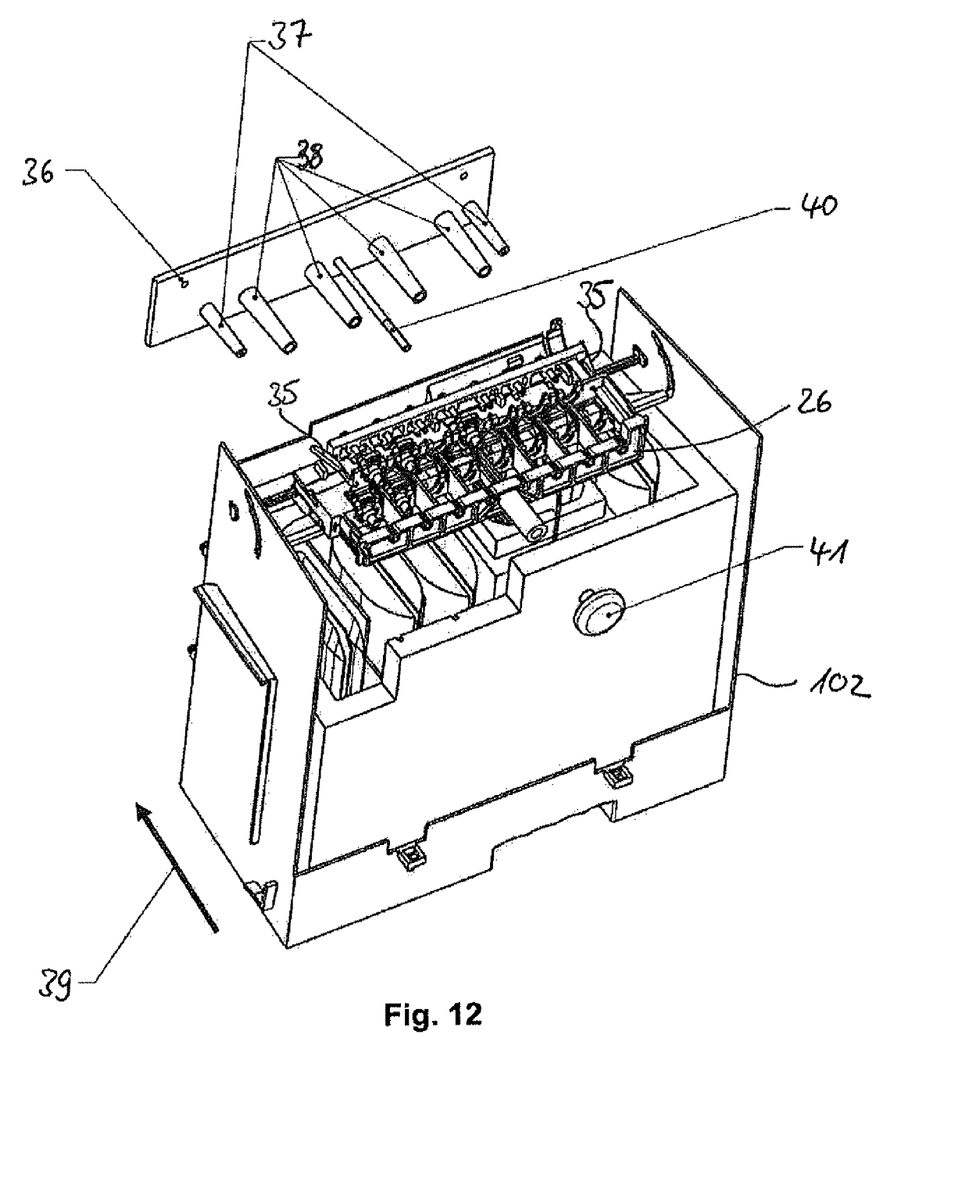
FIG. 12 is a representation of the cassette and a part of the base module interface, via which the cassette is connectable with the base module of the analyzer.

FIG. 12 shows the cassette 102 and a part of the base module interface 36, via which the cassette 102 is connectable with the base module 101 of the analytical device. During connecting of the cassette 102 with the base module 101, the support- and stop pins 38, through a shifting movement of the cassette 102 relative to the base module 101 in the direction of the arrow 39, enter into the housing 23 of the cassette 102 until they hit the second carrier block 28. Shortly therebefore, the two outer pins 37 of the interface 36 contact the levers 35 in such a way that the levers 35 are swung upwards and release the noses, so that the path is free for the added shifting of the first carrier block 27 in the direction of arrow 39 toward the second carrier block 28 for connection of the primary components 1 with the secondary components 2.

The carrier apparatus 26 includes a pressure plate 29, which is connected with a cartridge 30 arranged centrally on the rear-side of the pressure plate 29 facing away from the fluid coupling apparatuses 10 and extending perpendicular to the pressure plate 29. For lengthening the cartridge 30, there extends through the carrier apparatus 26 a bore 42, into which a screw 40 arranged on the interface 36 of base module enters, when the cassette 102 is connected as shown in FIG. 12 with the base module 101. During connecting of the cassette 102 with the base module 101, the screw 40 engages with the hand wheel 41 arranged frontally on the housing 23 of the cassette 102, so that, by rotation of the hand wheel 41, a shifting movement of the cartridge 30 and the pressure plate 29 connected with it in the direction of arrow 39 is brought about. The dimensions of the snap hook 33 arranged on the first carrier block 27 and a complementary groove of the second support 28 are so matched to one another that the snap hook 33 snaps in an end position into the groove, in which the primary components and the secondary components of the fluid coupling apparatuses 10 are connected fluid-tightly with one another, so that the transport of liquid between the liquid containers 25 and the measuring cell via the fluid coupling apparatuses is then possible.

The invention claimed is:

1. An analytical device for automated determining of a measured variable of a liquid sample, comprising:
   a base module;
   a measuring cell disposed within the base module;
   a fluid line connected to the measuring cell within the base module;
   a replaceable cassette connectable with said base module and including at least one liquid container disposed therein, the at least one liquid container connectable via said fluid line with said measuring cell and containing a reagent to be added to the liquid sample for forming a measured liquid;
   a measuring transducer for registering measured values correlated with the measured variable for the measured liquid accommodated in said measuring cell; and
   a fluid coupling apparatus disposed within said replaceable cassette and associated with said at least one liquid container, said fluid coupling apparatus having a primary component and an opposing secondary component, wherein the primary component and the secondary component each comprise an interface via which the primary component and the secondary component can be connected together to form a fluid tight connection and to provide a fluid communication between the at least one liquid container and the fluid line connected to the measuring cell,
   wherein the primary component includes a cartridge-shaped housing having a front opening and a rear opening and an interior, the front opening including a sealing seat on which lies a sealing element arranged in the housing interior, the sealing element embodied to reversibly close the front opening liquid tightly when the primary component is not connected with the secondary component, and
   wherein the rear opening is connected with the liquid container via another fluid line.

2. The analytical device as claimed in claim 1, wherein:
   said base module and said replaceable cassette are separate components configured to be mechanically connected; and
   said replaceable cassette includes snap fits structured to prevent movement of said secondary component relative to said primary component when said replaceable cassette is not connected with said base module, and to enable movement of said secondary component relative to said primary component upon the connecting of said replaceable cassette with said base module.

3. The analytical device as claimed in claim 1, wherein:
   said base module has a drive, the drive actuatable by hand or automatically, which is embodied to bring about movement of said secondary component and said primary component relative to one another for providing a fluid tight connection between said secondary component and said primary component.

4. The analytical device as claimed in claim 1, wherein:
   said secondary component has a cartridge-shaped plug that is structured to enter into said front opening of said housing of said primary component to displace the sealing element from its corresponding sealing seat to provide a fluid tight connection between said cartridge-shaped plug of said secondary component and the cartridge-shaped housing of said primary component.

5. The analytical device as claimed in claim 4, wherein said cartridge shaped plug of said secondary component has a cavity that, in the case of connected primary and secondary components, is disposed within said housing of said primary component.

6. The analytical device as claimed in claim 1, wherein said measuring cell is arranged in said base module.

7. The analytical device as claimed in claim 1, further comprising:
   at least one pump structured to transport liquid from said liquid container into said measuring cell and/or from said measuring cell into a liquid container; and
   a control unit comprising a data processor and a memory, in which one or more operating programs are stored and which is embodied to control said at least one pump and/or, based on measuring signals provided by said measuring transducer, to ascertain measured values of the measured variable.

8. The analytical device as claimed in claim 1, wherein the replaceable cassette comprises a cassette housing, and the at least one liquid container, the primary component and the secondary component are disposed within the cassette housing.

9. The analytical device as claimed in claim 1, wherein:
   said housing of said primary component tapers on its front end to form said seat; and
   a press part arranged in the interior of the housing and bearing on its rear side against an annular shoulder formed within the housing presses said sealing element against said sealing seat.

10. The analytical device as claimed in claim 1, wherein said sealing element is essentially spherically shaped.

11. The analytical device as claimed in claim 1, wherein:
    said housing of said primary component has a tapering section in a rear end region; and
    the interior of the housing includes at least one rib extending radially inwardly from a housing wall that prevents said sealing elements from being lifted from said sealing seats of said housing when the primary and secondary components are connected.

12. The analytical device as claimed in claim 1, wherein said primary component has a radially extending grip on an exterior of the housing.

13. An analytical device for automated determining of a measured variable of a liquid sample, comprising:
    a base module;
    a measuring cell disposed within the base module;
    a fluid line connected to the measuring cell within the base module;
    a replaceable cassette connectable with the base module and including a plurality of liquid containers disposed therein, the plurality of liquid containers connectable via the fluid line with the measuring cell, at least one liquid container containing a reagent to be added to the liquid sample for forming a measured liquid; and
    a measuring transducer for registering measured values correlated with the measured variable for the measured liquid accommodated in said measuring cell,
    wherein each of the plurality of liquid containers is associated with a corresponding fluid coupling apparatus disposed within the replaceable cassette, each fluid coupling apparatus including a primary component and an opposing secondary component,
    wherein each primary component and secondary component comprise an interface via which, when the replaceable cassette is connected with the base module, the primary component and secondary component make a fluid tight connection and enable fluid communication between each of the plurality of liquid containers and the fluid line connected to the measuring cell, wherein either the primary component or the secondary component of each fluid coupling apparatus is connected to its associated liquid container on an end opposite the interface, and wherein the primary components are mounted on a first carrier and the secondary components are mounted on a second carrier movable relative to said first carrier.

14. The analytical device as claimed in claim 13, wherein said first carrier and said second carrier are configured for mounting to one another in a guided relative movement of said first carrier and said second carrier achieving a connection of said carrier mounted to said primary and secondary components of said fluid coupling apparatuses.

* * * * *